(12) United States Patent
Chiu et al.

(10) Patent No.: US 8,927,696 B2
(45) Date of Patent: Jan. 6, 2015

(54) HUMANIZED ANTI-HUMAN CD34 MONOCLONAL ANTIBODY AND USES THEREOF

(71) Applicant: Industrial Technology Research Institute, Hsinchu (TW)

(72) Inventors: Wei-Chun Chiu, Zhubei (TW); Min-Yuan Chou, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 64 days.

(21) Appl. No.: 13/646,530

(22) Filed: Oct. 5, 2012

(65) Prior Publication Data
US 2013/0172533 A1 Jul. 4, 2013

(30) Foreign Application Priority Data

Dec. 29, 2011 (TW) .............................. 100149470 A

(51) Int. Cl.
*C07K 16/00* (2006.01)
(52) U.S. Cl.
USPC .................. 530/387.1; 530/388.1; 530/388.15
(58) Field of Classification Search
None
See application file for complete search history.

(56) References Cited

U.S. PATENT DOCUMENTS

| | | | |
|---|---|---|---|
| 4,714,680 | A | 12/1987 | Civin |
| 5,061,620 | A | 10/1991 | Tsukamoto et al. |
| 5,585,089 | A | 12/1996 | Queen et al. |
| 5,821,337 | A | 10/1998 | Carter et al. |
| 6,838,282 | B2 | 1/2005 | Lawman et al. |
| 2008/0187966 | A1 | 8/2008 | Simmons |
| 2010/0311955 | A1 | 12/2010 | Guo et al. |

FOREIGN PATENT DOCUMENTS

| | | |
|---|---|---|
| EP | 1 083 226 A1 | 3/2001 |
| WO | WO 99/61629 A1 | 12/1999 |
| WO | WO 2009/079922 A1 | 7/2009 |

OTHER PUBLICATIONS

Taiwanese Office Action for Taiwanese Application No. 100149470 dated Nov. 27, 2013.
Aoki et al., "Endothelial Progenitor Cell Capture by Stents Coated With Antibody Against CD34", The HEALING-FIM (Healthy Endothelial Accelerated Lining Inhibits Neointimal Growth-First in Man), Journal of the American College of Cardiology. vol. 45. No. 10. (2005) pp. 1574-1579.
Beschorner et al., "Localization of Hematopoietic Progenitor Cells in Tissue With the Anti-My-10 Monoclonal Antibody", Rapid Communication, Department of Pathology and the Division of Pediatric Oncology of the Oncology Center, JHU School of Medicine, Baltimore, MD. Apr. 1985, pp. 1-4.
Hou et al., "Humanization of an Anti-CD34 Monoclonal Antibody by Complementarity-determining Region Grafting Based on Computer-assisted Molecular Modelling", J. Biochem, 144, (2008), pp. 115-120.
Pedroso et al., "Improved Survival, Vascular Differentiation and Wound Healing Potential of Stem Cells Co-Cultured with Endothelial Cells", PLoS ONE, Jan. 2011, vol. 6, Issue 1, pp. 1-12.
Sato et al., "Purification of human marrow progenitor cells and demonstration of the direct action of macrophage colony-stimulating factor on colony-forming unit-macrophage", Retrieved from http://bloodjournal.hematologylibrary.org, on Jun. 7, 2012. pp. 967-974.
Shi et al., "Stem-cell-capturing collagen scaffold promotes cardiac tissue regeneration", Biomaterials 32 (2011) pp. 2508-2515.
Yin et al., "Combinatorial coating of adhensive polypeptide and anti-CD34 antibody for improved endothelial cell adhension and proliferation", Mater Med (2009) pp. 1513-1523.

*Primary Examiner* — Michail Belyavskyi
(74) *Attorney, Agent, or Firm* — Birch, Stewart, Kolasch & Birch, LLP.

(57) ABSTRACT

A novel humanized antibody against the CD34 surface antigen on the human stem cells is provided. The humanized antibody contains a heavy chain variable region comprising an amino sequence as set forth in SEQ ID No. 1 and a light chain variable region comprising an amino sequence as set forth in SEQ ID No. 2. The disclosure also provides the applications of the disclosed humanized antibody.

22 Claims, 10 Drawing Sheets hMy10 VH: EVQLVESGGG LVQPGGSLRL SCAVSGFSLT SHGVHWVRQA PGKGLEWLGV IWGAGRTDYN
AAFISRLSIS RDISKSQVYL QMNSLRAEDT AVYYCARNRY ESYFDYWGQG TLVTVSS hMy10 VL: DIQMTQSPSS LSASVGDRVT ITCRSSQNLV HSNGNTYLHW YQQKPGKAPK LLIYKVSNRF
SGVPDRFSGS GSGTEFTLTI SSLQPEDFAT YYCSQSTHVP LTFGQGTKVE IKR

FIG. 3

HUMANIZED ANTI-HUMAN CD34 MONOCLONAL ANTIBODY AND USES THEREOF

CROSS REFERENCE TO RELATED APPLICATIONS

This application claims the benefit of Taiwan Patent Application No. 100,149,470, filed Dec. 29, 2011. The disclosure of the application is incorporated herein by reference.

INCORPORATION BY REFERENCE OF SEQUENCE LISTING

A sequence listing submitted as a text file via EFS-Web is incorporated herein by reference. The text file containing the sequence listing is named "0965-A23832-US_Seq_Listing.txt"; its date of creation is Apr. 17, 2012; and its size is 3,464 bytes.

BACKGROUND

1. Technical Field

The technical field relates to a humanized anti-human CD34 monoclonal antibody and uses thereof.

2. Description of the Related Art

Human stem cells are a group of undifferentiated cells with the ability to undergo unlimited cell division and differentiation to various cell types, such as hematopoietic stem cells (HSCs). HSCs present in the human marrow and peripheral blood are capable of self-regeneration and differentiation to various cell types. Due to the monocyte-like morphology, HSCs had not been identified until the surface proteins were determined. The surface antigen, CD34, is a transmembrane glycoprotein expressed on the HSC membrane, with an identified molecular weight of about 110 kDa. CD34 has been the first developed biomarker for determining human HSCs (Civin, et al. 1984; Krause, D. S. et al. 1996). Due to the specific binding affinity to the CD34 surface protein, HSCs are capable of being isolated from human blood. The isolated HSCs are available for transplantation in the treatment of several diseases, such as malignant hematologic diseases and solid tumors. However, a success of HSC transplantation therapy raises an issue, how to obtain a sufficient quantity of purified HSCs from the blood (Shpall E J, et al. 1994).

In spite of HSCs, it has been studied that CD34$^+$ stem cells may differentiate to an endothelial type which is called endothelial progenitor cells (EPCs). Several studies have shown that EPCs promote neovascularization and re-endothelialization which correlate to the healing of cardiovascular disorders and wound recovery. Therefore, the way to increase the amount of EPCs or to capture EPCs from the blood is potential for development of medical instruments (Carmen U and Stefanie D, 2004; Jiro A, et al. 2005).

Accordingly, a development of efficient separation and purification of HSCs and EPCs is needed to increase their value in medicine, wherein the antibody-antigen specific binding might be a way to meet the purpose.

Anti-My10 monoclonal antibody (MAb) is a murine-derived antibody against human myeloid cell line KG-1a, which has high affinity and specificity to the CD34 antigen. Several studies have shown that anti-CD34 antibody is a potential MAb for isolation and identification of HSCs (Watt S M, et al., 1987; W. E. Beschorner et al. 1985). In recent researches, murine-derived MAbs have been used in the separation, capture and labeling of HSCs and EPCs. However, murine-derived MAbs may generate other problems. For example, murine-derived MAbs may depart from the isolation column when purifying HSCs from the peripheral blood and enter into the human body with HSC transplantation leading to undesired immune responses.

A major impediment for using murine-derived MAbs in clinical practice is that it may elicit human anti-murine antibody (HAMA) responses in patients (Owens and Young, 1994; Sandhu, 1992; Schroff et al., 1985). Hence, to improve efficiency in clinical use, genetic engineering technology has been employed to replace the murine content with the amino acid residues of human counterparts, which reduces the possibility of inducing immunogenicity in patients.

An ideal for antibody humanization is that it should be capable of maintaining specificity and affinity toward an antigen and reduce immunogenicity as much as possible. So far, many approaches have been used for antibody humanization, such as chimeric antibodies, which consists of murine antigen-binding variable regions fused genetically to human antibody constant regions. This was the earliest attempt to reduce immunogenicity (Morrison et al., 1984). However, chimeric antibodies would still generate undesirable anti-variable region responses (Bruggemann et al., 1989).

CDR-grafting is another approach involving the transfer of the complementarity determining regions (CDRs) from a rodent antibody to the Fv frameworks (FRs) of a human antibody (Verhoeyen et al., 1988). Unfortunately, the interface changes between CDRs and new FRs may largely disturb the binding to the antigen. The initial CDR-grafted antibodies tend to lose parental binding affinity, and therefore require additional work for back-mutation of several murine framework amino acids, which are regarded as crucial for CDR loop conformations. Thus, the method is not only time-consuming but results in a low probability of success.

As the development of structural biology, the murine antibody can be constructed in a three-dimensional structure on homology modeling and substitute the amino acid residues that possibly hinder the antigen binding in the murine Fv frameworks with the corresponding residues of human antibodies. This method maintains the advantages of humanization and eliminates HAMA responses, becoming a trend for antibody humanization.

SUMMARY

One embodiment of the disclosure provides a humanized monoclonal antibody, comprising a heavy chain variable region comprising an amino acid sequence as set forth in SEQ ID NO: 1 and a light chain variable region comprising an amino acid sequence as set forth in SEQ ID NO: 2, wherein the humanized monoclonal antibody specifically binds to the CD34 antigen on the surface of human cells.

Another embodiment of the disclosure provides a humanized monoclonal antibody, comprising a heavy chain variable region comprising an amino acid sequence encoded by a nucleotide sequence as set forth in SEQ ID NO: 3 and a light chain variable region comprising an amino acid sequence encoded by a nucleotide sequence as set forth in SEQ ID NO: 4, wherein the humanized monoclonal antibody specifically binds to the CD34 antigen on the surface of human cells.

In another embodiment, the disclosure provides a method for separating a cell with CD34 antigen, comprising: (i) providing a capturing molecule carrying the said humanized monoclonal antibody; (ii) mixing the capturing molecule with a bio-sample containing the cells with CD34 antigen, wherein the antibody binds to the CD34 antigen of the cell in the bio-sample to form a complex; and (iii) isolating the complex to obtain a cell carrying the surface antigen CD34.

In one more embodiment, the disclosure provides a method for labeling a cell with CD34 antigen, comprising: (i) providing a labeling molecule carrying the said humanized monoclonal antibody; and (ii) mixing the labeling molecule with a bio-sample containing the cell with CD34 antigen, wherein the antibody binds to the CD34 antigen in the bio-sample to label a cell carrying the CD34 surface antigen.

In another embodiment, the disclosure provides an imaging agent comprising the said humanized monoclonal antibody and a labeling material binding to the humanized monoclonal antibody.

In another embodiment, the disclosure provides a bead comprising the said humanized monoclonal antibody and a magnetic substrate carrying the antibody.

In another embodiment, the disclosure provides a device of cell capture, comprising a support containing a surface and the said humanized monoclonal antibody coated on the surface.

A detailed description is given in the following embodiments with reference to the accompanying drawings.

BRIEF DESCRIPTION OF THE DRAWINGS

The embodiments can be more fully understood by reading the subsequent detailed description and examples with references made to the accompanying drawings, wherein:

FIG. 3 shows the amino acid sequences of hMy10 IgG heavy chain variable region (hMy10 IgG $V_H$) and hMy10 IgG light chain variable region (hMy10 IgG $V_L$).

DETAILED DESCRIPTION

Figure 1:
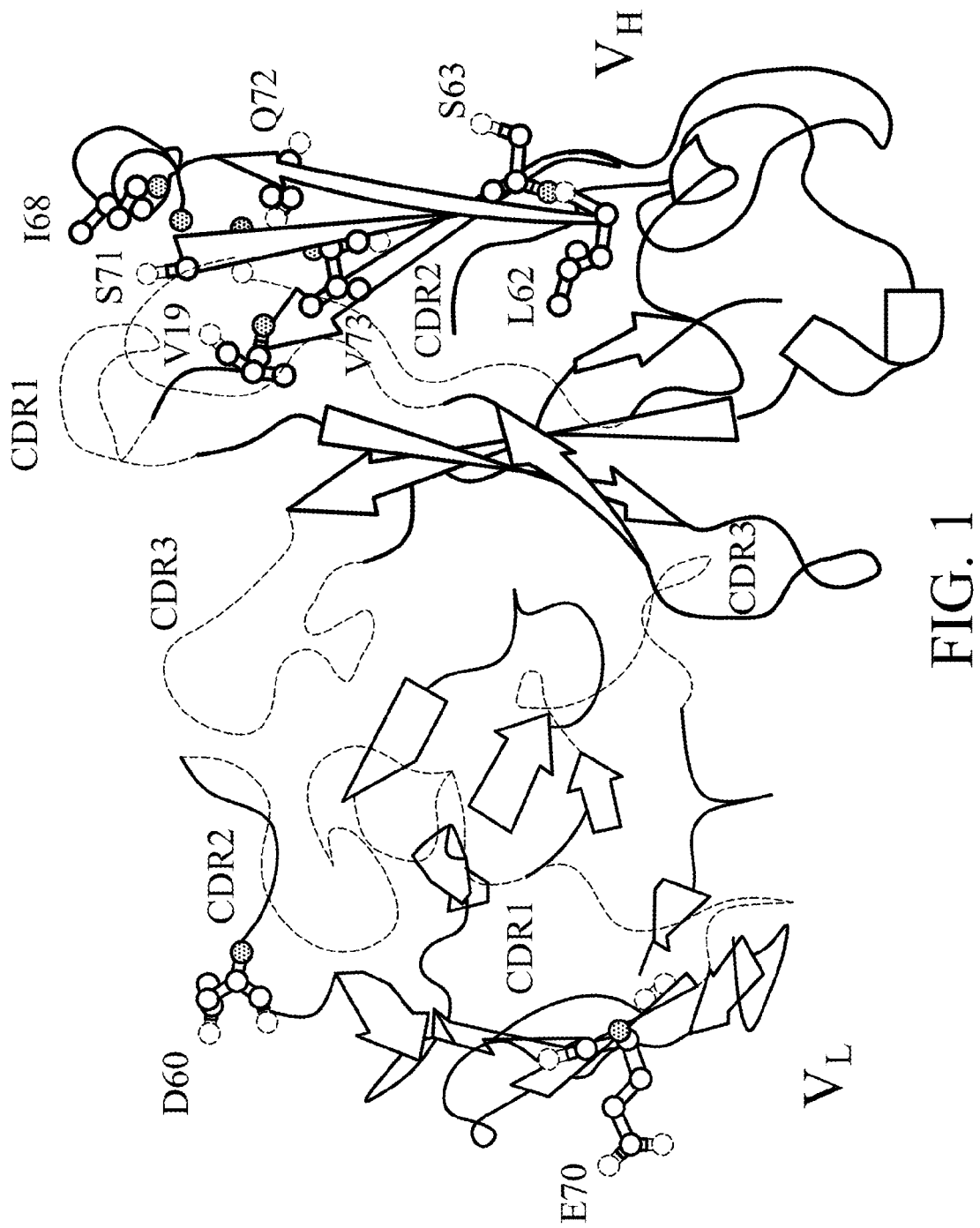
FIG. 1 shows the structure of mMy10 IgG heavy chain variable region and light chain variable region obtained from the homology modeling process.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to embodiments of the disclosure, the humanized monoclonal antibody is constructed through humanization of anti-My10 murine monoclonal antibody (mMy10 IgG). In one example, the humanization may comprise the following steps: (1) constructing a three-dimensional structure of mMy10 IgG according to a homology modeling process and determining amino acid residues relating to the antigen binding; and (2) reserving the amino acid residues crucial for the antigen binding in the mMy10 IgG variable regions and grafting these residues to human antibody frameworks through the CDR-grafting process. In this example, the homology of the amino acid sequences in the mMy10 IgG variable region was determined under computer software analyses of the homology modeling process. According to prior studies, the mMy10 IgG variable region in a three-dimensional structure was constructed as shown in FIG. 1. In FIG. 1, the region in thick lines at the right hand side refers to the heavy chain variable region ($V_H$), and the region in thin lines at the left hand side refers to the light chain variable region ($V_L$). The dotted line between $V_H$ and $V_L$ refers to the CDR region, and the spheres refer to the amino acid residues relating to the antigen binding, which is considered as being reserved.

In the example, cDNAs corresponding to the amino acid sequences in the variable region of the humanized My10 IgG were synthesized according to the result of the homology modeling. The cDNAs were then recombinant with human $IgG_1$ frameworks and transfected into a cell expressing the humanized My10 IgG (hMy10 IgG) antibodies.

According to embodiments of the disclosure, the humanized antibody contains: (a) the heavy chain variable region comprises an amino acid sequence as set forth in SEQ ID NO: 1 or an amino acid sequence encoded by a nucleotide sequence as set forth in SEQ ID NO: 3; and (b) the light chain variable region comprises an amino acid sequence as set forth in SEQ ID NO: 2 or an amino acid sequence encoded by a nucleotide sequence as set forth in SEQ ID NO: 4. According to embodiments of the disclosure, the binding affinity of the humanized antibody reaches to an extent of nanomoles, indicating that the humanized antibody is applicable for various purposes.

Accordingly, the said humanized monoclonal antibody in one embodiment of the disclosure specifically binds to the CD34 surface antigen of human cells, particularly for human stem cells, hematopoietic stem cells (HSCs) and stem cell-differentiated endothelial progenitor cells (EPCs).

In addition, the humanized monoclonal antibody according to embodiments of the disclosure is capable of reducing human anti-murine antibody (HAMA) responses which often occur in the use of murine-derived antibodies, and increasing the clinical biosafety.

In one embodiment, the disclosure provides a method for cell separation, comprising providing a capturing molecule carrying the said humanized monoclonal antibody; mixing the capturing molecule with a biosample, wherein the antibody binds to a CD34 cell-surface antigen in the biosample to form a complex; and isolating the complex to obtain a cell carrying the CD34 surface antigen.

In this embodiment, the capturing molecule carrying the humanized monoclonal antibody may comprise a solid support, functional group or biomolecule, but is not limited thereto. The solid support recited herein may comprise a bead, microchip, microplate or the like. The solid support may be modified with functional groups or biomolecules for binding to the antibody. The functional group may comprise an amino group (—$NH_2$), mercapto group (—SH), carboxyl group (—COOH), hydroxyl group (—OH) or the like. The biomolecule recited herein may comprise biotin, avidin, streptavidin or a biomolecule with a binding affinity to the said antibody. The bead in the embodiment may comprise commercially available iron oxide particles (IOP), superparamagnetic iron oxide particles (SPIO) or other magnetic micro- or nano-beads. In one example, the capturing molecule is a bead modified with an anti-biotin molecule on the surface, binding to the biotinylated humanized antibody. In this example, the isolation of the complex consisting of the capturing molecules and bound cells may be performed under the bead isolation process. For instance, the isolation occurs from magnetically attracting the beads with a strong magnetic separator.

In one embodiment of the disclosure, the method for cell separation may further comprise a dying step, comprising adding a dyed antibody. The dyed antibody carrying a coloring material is capable of binding the said humanized antibody. The coloring material may comprise fluorochromes, such as fluorescein isothiocyanate (FITC), Alexa Fluor dye, cyanine dye (cyanine dye, C2, Cy3 and Cy5) or the like; fluorescent proteins, such as phytochrome-based near-infrared fluorescent protein (iRFP); bioluminescences, such as firefly luciferase (Fluc) or Gaussia luciferase (Gluc); or nanoparticles, such as quantum dots, iron oxide magnetic beads (IOP), superparamagnetic iron oxide beads (SPIO) or the like. In one example, the dyed antibody is a commercially available Alexa fluor 647 labeled goat anti-human IgG antibody, but the disclosure is not limited thereto.

In this embodiment, the isolated cells, such as human stem cells, hematopoietic stem cells (HSCs) and endothelial progenitor cells (EPCs), may be further used for autologous transplantation of blood stem cells for the treatment of cardiac disorders and strokes.

In another embodiment, the disclosure provides a bead comprising the said humanized monoclonal antibody and a magnetic substrate carrying the antibody. The magnetic substrate may be modified with a functional group or biomolecule on the surface for binding to the antibody. The bead may comprise commercially available iron oxide magnetic bead (TOP), superparamagnetic iron oxide beads (SPIO) or the like. The functional group may comprise amino (—NH$_2$), mercapto (—SH), carboxyl (—COOH) or hydroxyl (—OH), but is not limited thereto. The biomolecule may comprise biotin, avidin, streptavidin, or the like. According to the properties of the magnetic substrate, the bead can be applied for cell isolation, purification, capture, labeling and imaging, in particular for the cell carrying the CD34 surface antigen, such as human stem cells, human hematopoietic stem cells (HSCs) and endothelial progenitor cells (EPCs).

In another embodiment, the disclosure provides a method for labeling cells, comprising: (i) providing a labeling molecule carrying the humanized monoclonal antibody; and (ii) mixing the labeling molecule with a biosample, wherein the antibody binds to a CD34 cell-surface antigen in the biosample for labeling a cell carrying the CD34 surface antigen. In the embodiment, the labeling molecule may comprise a color material or radioactive material that is capable of binding the antibody. The color material may comprise a fluorochrome, such as fluorescein isothiocyanate (FITC), Alexa Fluor dye or Cyanine dye (C2, Cy3 and Cy5); fluorescent protein, such as phytochrome-based near-infrared fluorescent protein (iRFP); bioluminescence, such as firefly luciferase (Fluc) or Gaussia luciferase (Gluc); nanoparticles, such as quantum dots, iron oxide magnetic beads or superparamagnetic iron oxide beads. The radioactive material may comprise $^{90}$Y, $^{111}$In, $^{131}$I or the like. Due to the antigen-antibody binding affinity, the cells carrying the CD34 surface antigen, such as human stem cells, hematopoietic stem cells (HSCs) or endothelial progenitor cells (EPCs), would be labeled under the process so that the cell activity and morphology can be clearly observed for research, physical diagnoses and disorder treatments.

In another embodiment, the disclosure provides an imaging agent comprising the said humanized monoclonal antibody and a labeling material binding to the humanized monoclonal antibody. In this embodiment, the labeling material may comprise a color material or radioactive material which is capable of binding the antibody. The color material may comprise a fluorochrome, such as fluorescein isothiocyanate (FITC), Alexa Fluor dye or Cyanine dye (C2, Cy3 and Cy5); fluorescent protein, such as phytochrome-based near-infrared fluorescent protein (iRFP); bioluminescence, such as firefly luciferase (Fluc) or Gaussia luciferase (Gluc); nanoparticles, such as quantum dots, iron oxide magnetic beads or superparamagnetic iron oxide beads. The radioactive material may comprise $^{90}$Y, $^{111}$In, $^{131}$I or the like. The imaging agent according to the disclosure is useful in the cell fluorescence or luminescence, quantitative positron emission tomography (PET), computed tomography (CT scan), radionuclide imaging or magnetic resonance imaging (MRI) for detecting disorders or symptoms relevant to the human cells carrying the CD34 surface antigen.

Figure 9:
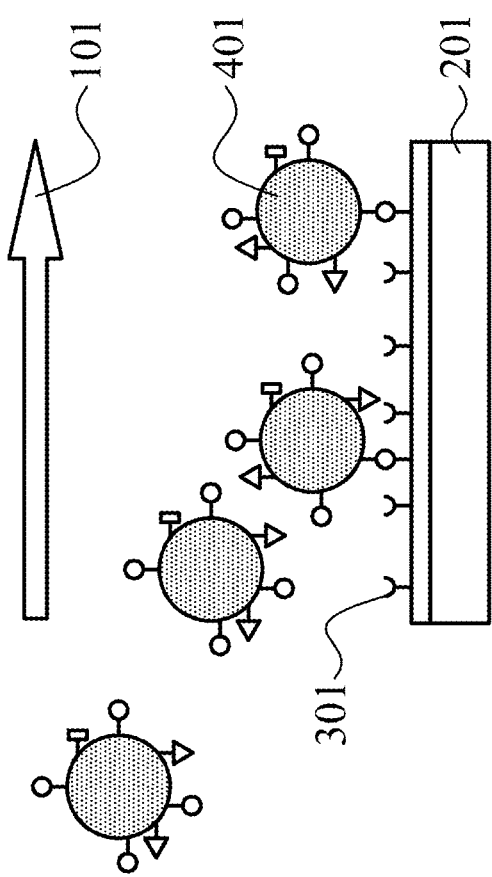
FIG. 9 shows a device for cell capture according to an embodiment.

In another embodiment, the disclosure provides a device for cell capture comprising a support containing a surface and the said humanized monoclonal antibody coated on the surface for capturing a human cell carrying the CD 34 surface antigen. One example of the device for cell capture is depicted in FIG. 9. According to FIG. 9, the device for cell capture comprises a support (201) which contains a surface coated with the humanized monoclonal antibody (301). When the blood flows (101) through the surface coated with the said antibody, the endothelial progenitor cells (EPCs) (401) carrying the surface antigen CD34 in the blood will be captured on the device. Therefore, the device can be a medical instrument in contact with the blood flow, such as coronary stent, cardiac catheter or the like. In cases where a coronary stent or cardiac catheter is used as the body of the device, the capture of cells carrying the CD34 surface antigen may inhibit the thrombus formation and increase the biocompatibility of the device.

EXAMPLES

Materials and Methods

A. Homology Modeling of Murine My10 Antibody

The homology modeling process of murine My10 IgG binding to the CD34 surface antigen of human hematopoietic stem cell was performed by using a Discovery Studio Modeling 2.1 (Accelrys, Inc., SanDiego, Calif.).

The amino acid sequences of mMy10 IgG variable regions were obtained from Chris A., et al. 1996. Two separate BLASTP searches were performed for the light chain variable region ($V_L$) and the heavy chain variable region ($V_H$) of mMy10 IgG. For identifying the homology of the amino acid sequences of the mMy10 variable regions, the sequences were analyzed by searching over the Protein Data Bank (PDB) (http://www.rcsb.org/pdb/home/home.do). According to the $V_H$ domain of the murine anti- the N type blood group antibody Fab fragment [PDB etry:1T2Q] (Xie, K. et al., 2004) and $V_L$ domain of the anti-human carbonic anhydrase IX antibody [PDB etry:2HKH] (Kral, V. et al., 2008), a three-dimensional structure of the mMy10 F$_V$ fragment was constructed. A final three-dimensional model was generated by a MODELLER module (Sali et al., 1995), which implements an automated approach to comparative protein structure modeling by satisfaction of spatial restraints. Automatic protein homology modeling and loop modeling for mMy10 IgG were performed. Model building of the CDR loops was performed by selecting template structures from the PDB database with the highest sequence identity using the Model antibody Loops module and refined using the Loop Refinement module in order to minimize steric clashes and ensure correct bond lengths and angles. Note that the model may be further refined by using a CHARMm (B. R. Brooks, 1983) with an Accelrys CHARMm forcefield in the Discovery Studio Modeling 2.1 for energy minimization. If so, the structure is energy-minimized in two steps. First, by 5000 steps of restrained steepest descent minimization, and next, by another 5000 steps of conjugated gradient minimization, while the alpha carbons of the framework are held in a fixed position.

B. Production and Purification of mMy10 IgG Antibody

A hybridoma HB-8483 (purchased from ATCC) producing a mMy10 IgG antibody binding to the surface antigen CD34 of human hematopoietic stem cell was cultured in a non-serum medium Hybridoma-SFM (GIBCO, 12045). The cultured supernatant was purified through Protein A column (GE Health-care) and the mMy10 IgG binding to the surface antigen CD34 of human hematopoietic stem cell was obtained.

C. Construction, Expression and Purification of hMy10 IgG

According to the humanization result with the amino acid sequences of the humanized My10 IgG variable regions, GeneDirex Inc., USA was authorized to synthesize the DNA sequences of $V_H$ and $V_L$ of the hMy10 IgG. The constant region sequences which came from human $IgG_1$ and the synthesized $V_H$ and $V_L$ sequences were subcloning into the mammalian expression vectors pSecTag2/Hygro (heavy chain) (Invitrogen) and pcDNA3.3-TOPO TA (light chain) (Invitrogen). The two constructs were then fused at the EcoRV restriction site to form a recombinant pSec-pcDNA-hMy10-IgG. Plasmids containing the heavy and light chain genes were transfected into mouse myeloma NS0 cells (European Collection of Animal Cell cultures, Salisbury, Wiltshire, UK) using Effectene (Qiagen) according to manufacturer's instructions. After selection with Hygromycin (400 µg/ml) for 4 weeks, a stable clone was cultured in a shaker flask at an initial seeding density of $5 \times 10^5$ cells/ml in a serum free chemically-defined medium HyQNS0 (Hyclone). Media was harvested for 5 days at 37° C. and antibodies were purified from the supernatant by Protein A (GE Health-care) chromatography.

D. Ability of hMy10 IgG and mMy10 IgG Binding to KG1a Cells

KG1a cells expressing the surface antigen CD34 were used for determining the antibody binding affinity. The antibody in aliquots were individually added into KG1a cells (about $1 \times 10^6$ cells) and reacted at 4° C. for 1 hour. The cells were washed with the FACS buffer (DPBS buffer with 2% fetus bovine serum) three times and then treated with the goat anti-mouse IgG (H+L) Alexa Fluor 488 responsive to mMy10 IgG and the goat anti-human IgG (H+L) Alexa Fluor 647 responsive to hMy10 IgG at 4° C. for 1 hour. The cells were further washed with the FACS buffer and analyzed under the FACSCalibur flow cytometer.

E. Binding Affinity of hMy10 IgG and QBen10 IgG to KG1a Cells

The antibody in aliquots were individually added into KG1a cells (about $1 \times 10^6$ cells) and reacted at 4° C. for 1 hour. The cells were washed with the FACS buffer (DPBS buffer with 2% fetus bovine serum) three times and then treated with the goat anti-mouse IgG (H+L) Alexa Fluor 488 responsive to QBen10 IgG and the goat anti-human IgG (H+L) Alexa Fluor 647 responsive to hMy10 IgG at 4° C. for 1 hour. The cells were further washed with the FACS buffer and analyzed under the FACSCalibur flow cytometer.

F. $CD34^+$ Cells Separation with Immunomagnetic Beads Carrying hMy10 IgG

The immunomagnetic beads carrying hMy10 IgG was prepared with EX-Link NHS-Biotin Reagents (Thermo Scientific Inc., Sample No. 20217) and anti-biotin beads (Miltenyi Biotec Inc., Sample No. 130-090-485). In brief, 1 mg of hMy10 IgG was added to a suitable amount of the biotin reagent (Thermo) and reacted on the ice for 2 hours. The reactant containing biotinylated hMy10 IgG antibodies was dialyzed with the PBS buffer to remove free biotins. In the other side, $CD34^-$ NS0 cells and $CD34^+$ KG1a cells were mixed at a ratio of 10:1 ($1 \times 10^7$ NS0 cells:$1 \times 10^6$ KG1a cells). The cell mixture was then added with the biotinylated hMy10 IgG antibodies and reacted at 4° C. for 30 minutes. The cells were washed with the MACS buffer three times. 80 µl of the MACS buffer and 20 µl of the Anti-Biotin Microbeads (MACS) were added and reacted at 4° C. for 15 minutes. The detection antibody, goat anti-human IgG (H+L) Alexa Fluor 647, was then added and reacted at 4° C. for 30 minutes. The cells were washed with the MACS buffer three times for the next steps set as the cell before separation.

The MS column and MiniMACS separator (MACS Inc.) were used for cell separation according to manufacturer's instructions. In brief, the MS column was set on the magnetic base of the MiniMACS separator. The MS column was balanced with 500 µl of the MACS degassed buffer.

The cells above were added into the MS column and washed with 500 µl of the MACS buffer three times to collect the flow-though fraction. Subsequently, the MS column was moved from the magnetic base and washed with 1 ml of the MACS buffers to elute the beads carrying the target cells. Finally, the cells before separation, the flow-through fraction and the eluted fraction were analyzed by FACSCalibur flow cytometer.

G. Capturing $CD34^+$ Cells by Using hMy10 IgG

A 96-well plate was coated with goat anti-human IgG antibody Fc fragments and put at 4° C. overnight. The plate was then washed with the PBST buffer three times. The blocking buffer (300 µl/well) was added and reacted at 37° C. for 1 hour. The plate was washed with the PBST buffer three times. Subsequently, the hMy10 IgG antibody in aliquots (4 µg/ml~0 µg/ml) was added and reacted at 37° C. for 1 hour. The plate was washed with the PBST buffer three times. Each well was added with $1 \times 10^5$ cells and the plate was under 20 rpm vibration at 37° C. for 1 hour. The unbound cells were washed out with the FACS buffer (DPBS buffer with 2% fetus bovine serum). The bound cells were detected with the Almar Blue assay and the percentage of the bound/unbound cells was calculated based on the control (0~5000 cells/well shown in the Almar Blue fluorescent dye).

H. $CD34^+$ Cell Capture in the Blood Flow on a Dynamic Modeling

A µ-slide (Ibidi) was coated 2 µg/ml of hMy10 IgG antibodies and reacted at 4° C. overnight. The slide was washed with the FACS buffer three times.

In the other side, $1 \times 10^6$ $CD34^+$ KG1a cells were labeled with the PKH67 Fluorescent Cell Linker Kit in advance. $1 \times 10^7$ $CD34^-$ NS0 cells were then added into the labeled KG1a cells and mixed uniformly. The cell mixture was then moved through the antibody-coated µ-slide with a peristaltic pump at room temperature for 2 hours. Thereafter, the FACS buffer was moved through the g-slide with a peristaltic pump to remove the unbound cells. The cells captured on the slide were observed under fluorescent microscope.

Results

A. Molecular Modeling on the mMy10 IgG Variable Region Fragments

The amino acid sequences in the mMy10 IgG variable regions were obtained from the prior studies. The three-dimensional structure of the deduced amino acid sequences in the $V_H$ and $V_L$ domains of mMy10 IgG was constructed individually by homology modeling (program MODELLER) as described under "Material and Methods." Afterward, the $V_H$ and $V_L$ domains of mMy10 IgG were modeled against the template structures 1T2Q (sharing 84% in sequence identity) at 2.50 Å resolution and 2HKH (sharing 94% in sequence identity) at 2.20 Å resolution from PDB, respectively. The final refined structures of the $V_H$ and $V_L$ domains of mMy10 IgG were obtained through a Discovery Studio modeling 2.1 program as shown in FIG. 1.

FIG. 1 shows the mMy10 IgG variable regions. The three-dimensional structure of mMy10 IgG was generated under homology modeling, by comparing the crystal structures of a 1T2Q for a $V_H$ domain and a 2HKH for a $V_L$ domain, respectively. The thick lines at the right hand side refer to the heavy chain variable region, while the thin lines at the left hand side refer to the light chain variable region. The loops in dotted lines refer to the CDR regions. The residues near the CDR loops within 5 Å shown as spheres are suggested involving in the antibody binding and considered being reserved, which are supposed crucial for CDR loop conformations and the antibody binding affinity. The residues shown as spheres comprise 7 residues of V19, L62, S63, I68, S71, Q72 and V73 in the heavy chain variable region and two residues of D60 and E70 in the light chain variable region. The reserved murine residues comprise nine Fv framework residues (FR), in which seven residues in the $V_H$ framework and two residues in the $V_L$ framework.

B. Humanization of mMy10 IgG Variable Fragments

Figure 2:
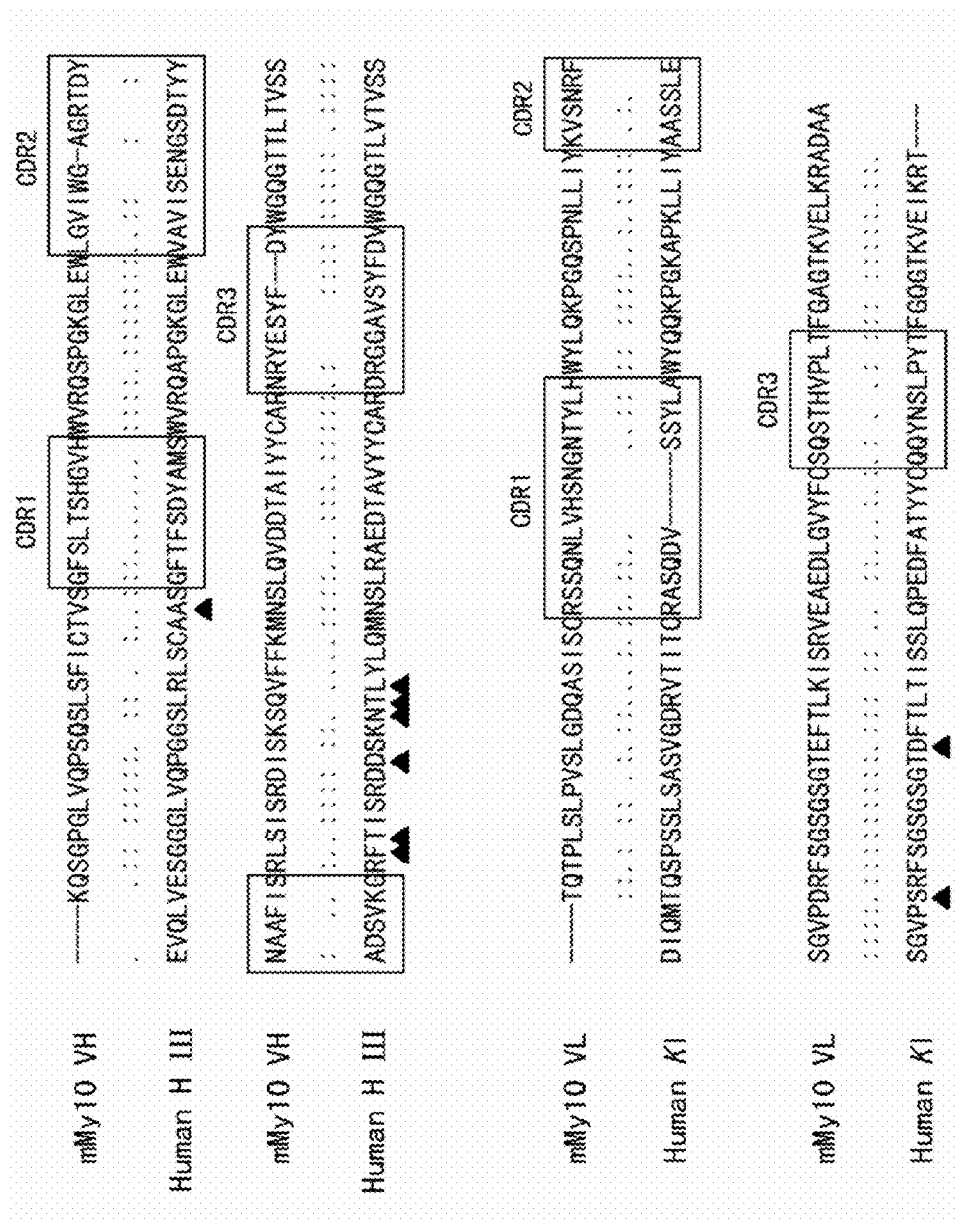
FIG. 2 shows the amino acid alignments of mMy10 IgG heavy chain variable region (mMy10 IgG $V_H$) with human $V_H$ subclass III (Human H III) heavy chain variable region and mMy10 IgG light chain variable region (mMy10 IgG $V_L$) with human $V_L$ k subclass I (Human K I) light chain variable region.

The CDR-grafting for the production of humanized murine-derived antibody has been well known in biotechnology and has been approved by the FDA. Clinical studies have shown that the CDR-grafting humanized antibody decreases the immunogenicity. However, the CDR-grafting usually results in a dramatic decrease of the antibody activity so that it is needed to recover some murine framework residues which are necessary in the CDR region stabilization. With the assistance of the structure homology modeling, the crucial murine framework residues around the CDR region can be more easily determined in order to keep the antibody activity. In brief, the mMy10 IgG humanization was performed in three steps in this example. First, the homolog models of the $V_H$ and $V_L$ domains of mMy10 IgG were constructed individually. Second, the residues near the CDR loops within 5 Å were determined according to the homolog models, suggesting that these residues impacted the antibody-antigen binding activity. Third, for selection of the residues in the variable regions, the most conserved human sequences, the first subclass of human $V_L$ k and the third subclass of human $V_H$, were set as templates of the human variable regions (Paul C. et al., 1992), and seven residues, V19, L62, S63, I68, S71, Q72 and V73, in the mMy10 IgG heavy chain and two residues, D60 and E70, in the mMy10 IgG light chain were reserved in the humanized antibody (FIG. 2). In the FIG. 2, the residues enclosed within rectangles refer to the CDR regions, and the residues pointed with the massive triangles refer to the residues critical for the antibody binding affinity, which are considered as being reserved. The rest of the humanized antibody used the human variable region as a template to form the hMy10 IgG variable regions as shown in FIG. 3. The most conserved human sequences in the heavy chain and the light chain had 52% and 51% in the sequence identity to the corresponding murine sequences, respectively.

C. Production and Purification of mMy10 IgG Antibody

Figure 4:
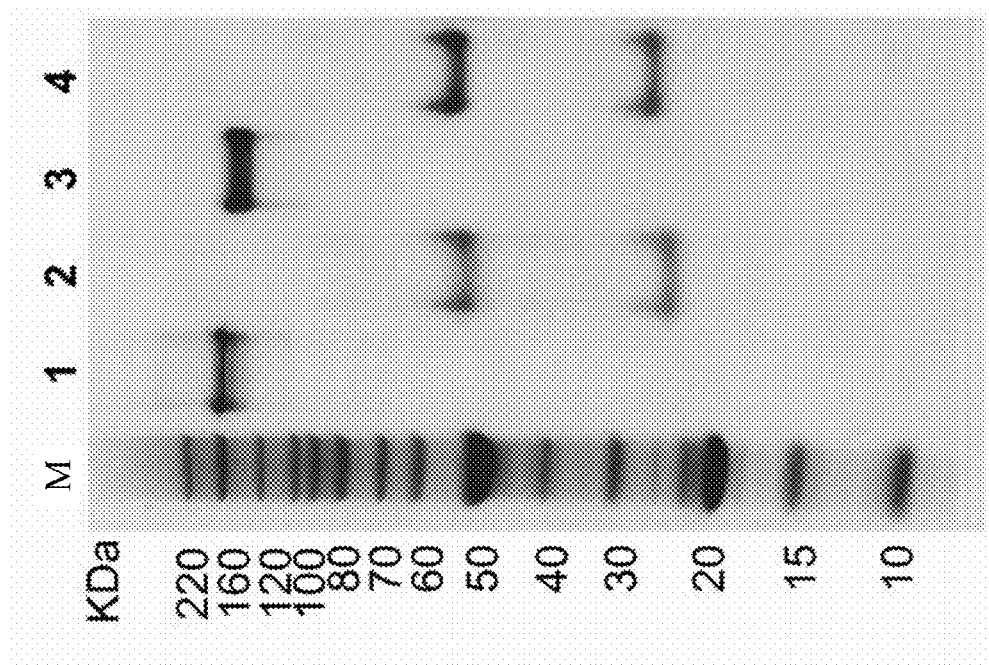
FIG. 4 shows the purified mMy10 IgG and hMy10 IgG on the SDS-PAGE assay according to an embodiment.

The purified mMy10 IgG was analyzed with SDS-PAGE and showed as FIG. 4. The samples containing mMy10 IgG and hMy10 IgG were performed in SDS/bis-tris polyacrylamide gel (4~12%) electrophoresis with MES buffers. Lane M refers to a molecular weight marker. Lanes 1 and 2 show mMy10 IgG in non-reduced and reduced forms, respectively. Lane 3 and 4 show hMy10 IgG in non-reduced and reduced forms, respectively. Lane 1 referred to the unreduced form with about 155 kDa and lane 2 referred to the reduced form with about 55 kDa (heavy chain) and 26 kDa (light chain).

D. Construction, Expression and Purification of hMy10 IgG

The amino acid sequences of the humanized $V_H$ and $V_L$ of mMy10 IgG were in-frame fused to the human $IgG_1$ heavy chain and kappa light chain constant regions, respectively. For the expression of an intact humanized My10 (hMy10) $IgG_1$ molecule, two different mammalian expression vectors, pSecTag2/Hygro and pcDNA3.3-TOPO TA, were used to express the humanized heavy chain and light chain of hMy10 IgG, respectively. Then, the light chain expression vector pcDNA3.3-TOPO TA was ligated to the heavy chain expression vector pSecTag2/Hygro. The expression level of the recombinant hMy10 IgG was about 13 mg/L. The culture medium containing hMy10 IgG was purified with protein A chromatography, and the protein purities were determined by the SDS-PAGE (FIG. 4). As shown in FIG. 4, hMy10 in a non-reduced form showed a single band with a molecular mass of 155 kDa (lane 3), while hMy10 in a reduced form yielded two protein bands with molecular masses of 55 kDa (heavy chain) and 26 kDa (light chain) (lane 4).

E. Binding Affinity of hMy10 IgG and mMy10 IgG to KG1a Cells

Figure 5:
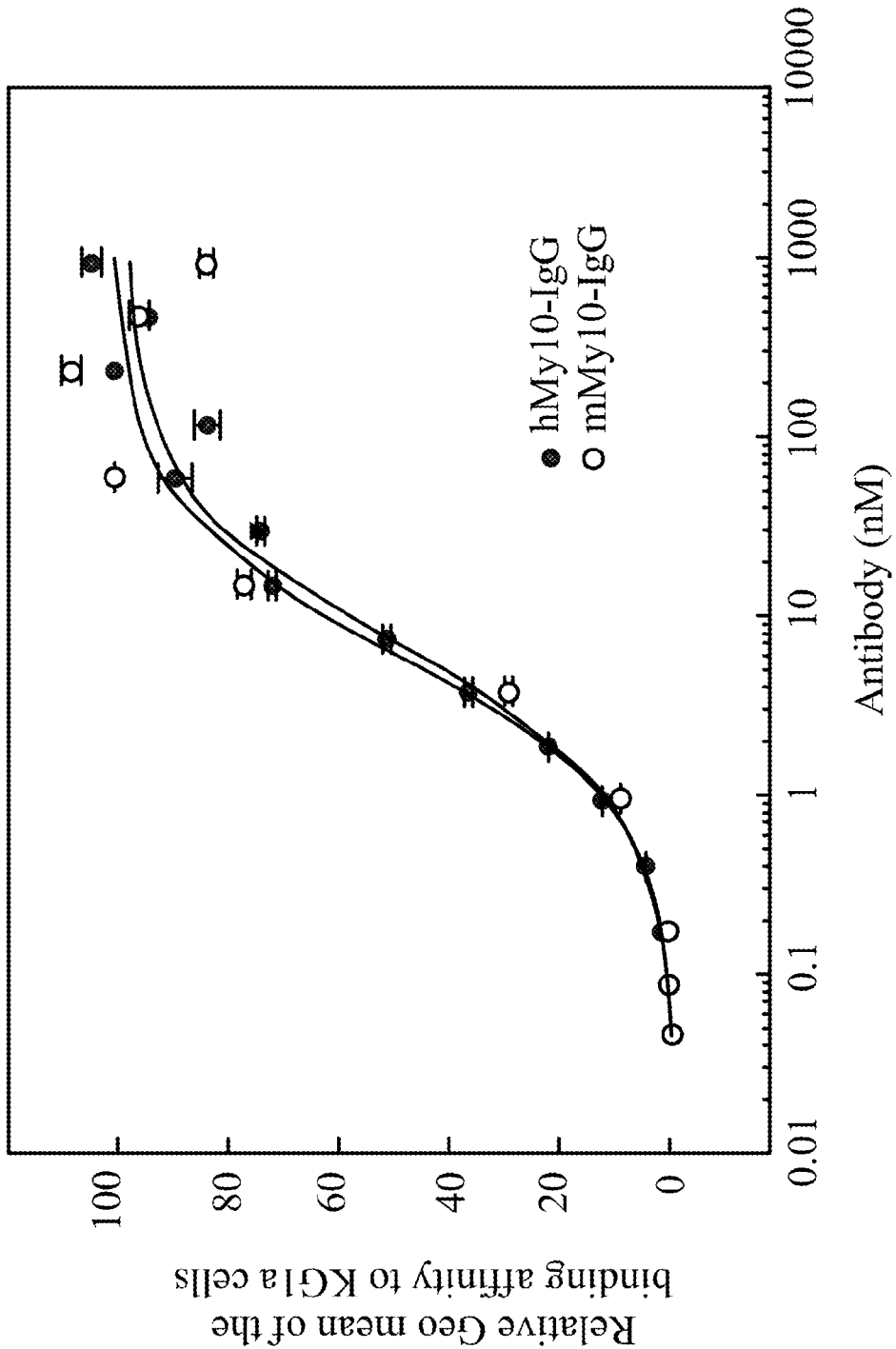
FIG. 5 shows the binding affinity of mMy10 IgG and hMy10 IgG to $CD34^+$ KG1a cells in a two-fold dilution according to an embodiment.

For determining the binding affinity of hMy10 IgG and mMy10 IgG to the surface antigen CD34 of human stem cells, a KG1a cell line was used as the cell expressing the surface antigen CD34. The binding affinity of the two antibodies to KG1a cells was observed at various antibody concentrations and estimated under flow cytometer. The result was shown in FIG. 5. The binding of the two antibodies to KG1a cells was dose-dependent, in which mMy10 IgG showed a $K_D$ value of 6.7 nM and hMy10 IgG showed a $K_D$ value of 6.9 nM. Both antibodies showed similar $K_D$ values, indicating that the humanization did not alter the binding affinity of My10 IgG to CD34 on the surface of human stem cells.

F. Binding Affinity of hMy10 IgG and QBen10 IgG to KG1a Cells

Figure 6:
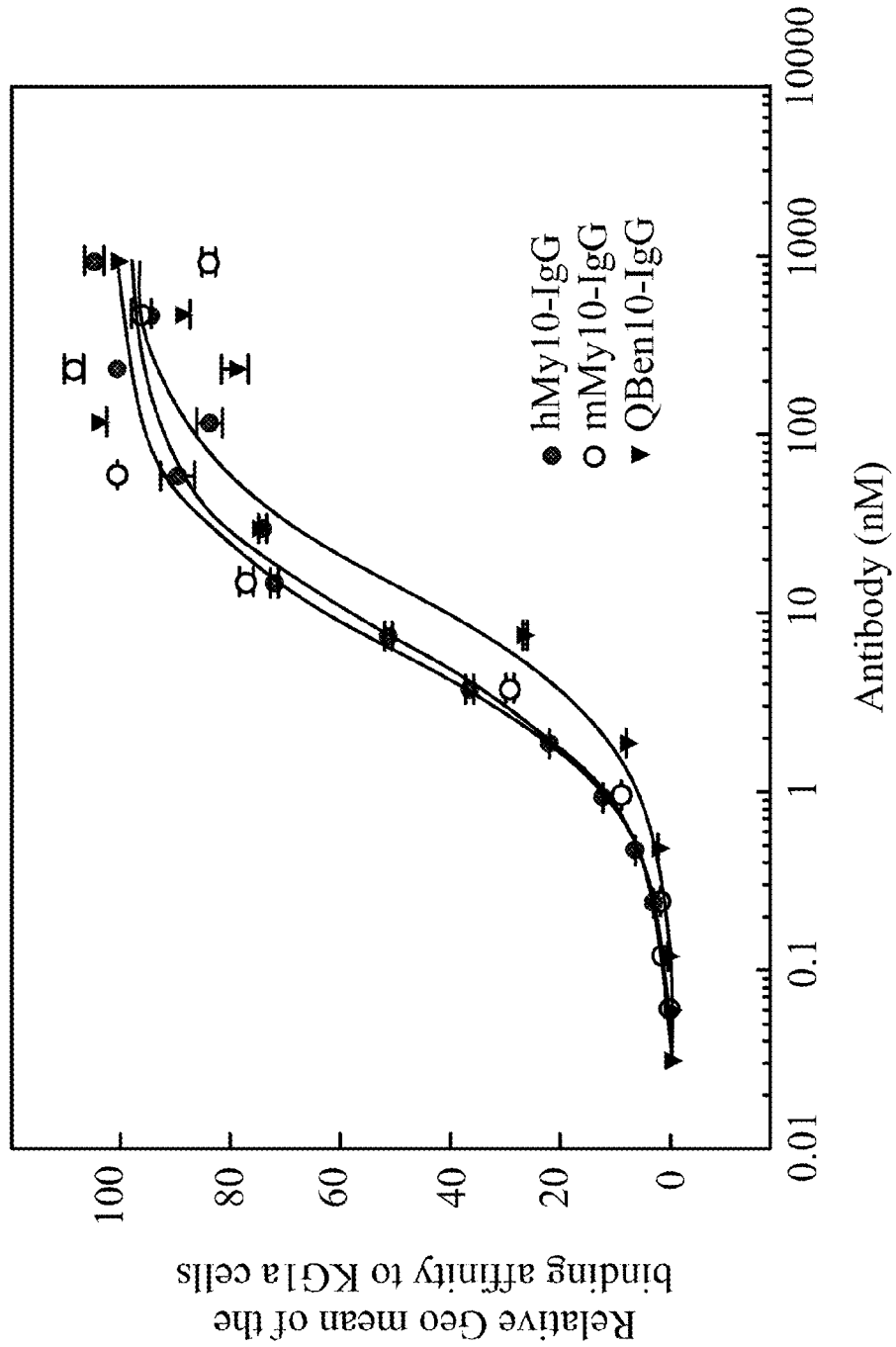
FIG. 6 shows the binding affinity of QBen10 IgG, mMy10 IgG and hMy10 IgG to $CD34^+$ KG1a cells according to an embodiment.

QBen10 IgG was a commercially available murine-derived antibody for detecting and isolating human stem cells carrying CD34 on the cell surface. The binding affinity of hMy10 IgG and QBen10 IgG to KG1a cells was studied above, showing that QBen10 IgG had a $K_D$ value of 14.4 nM in FIG. 6. The result indicated that binding affinity of hMy10 IgG to the surface antigen CD34 of human stem cells was similar to that of QBen10 IgG, while the humanized antibody has advantages on the immunogenicity with an increased applicability and value in medicine.

G. $CD34^+$ Cell Separation with Immunomagnetic Beads Carrying hMy10 IgG hMy10 IgG was determined for the stem cell separation from the peripheral blood or umbilical cord blood. In the study, the biotinylated hMy10 IgG was added into a cell mixture consisting of $CD34^-$ NS0 cells and $CD34^+$ KG1a cells at a ratio of 10:1. Anti-Biotin MicroBeads and the goat anti-human IgG (H+L) Alexa Fluor 647 as the detection antibody were then added. The cell separation was performed on the separator and the fractions collected at various timings were analyzed with FACSCalibur flow cytometer. The cell mixture before separation showed two types of cells, CD34− NS0 cells with no signal (left side) and CD34+ KG1a cells with signals (right side). The flow-through fraction showed no signal CD34− NS0 cells, while the CD34+ KG1a cells bound to the immunomagnetic beads showed signals in the eluted fraction. The yield (recovery) of KG1a cells was 80% relevant to the total cell number of KG1a cells initially added and the purity was 97%.

Figure 7:
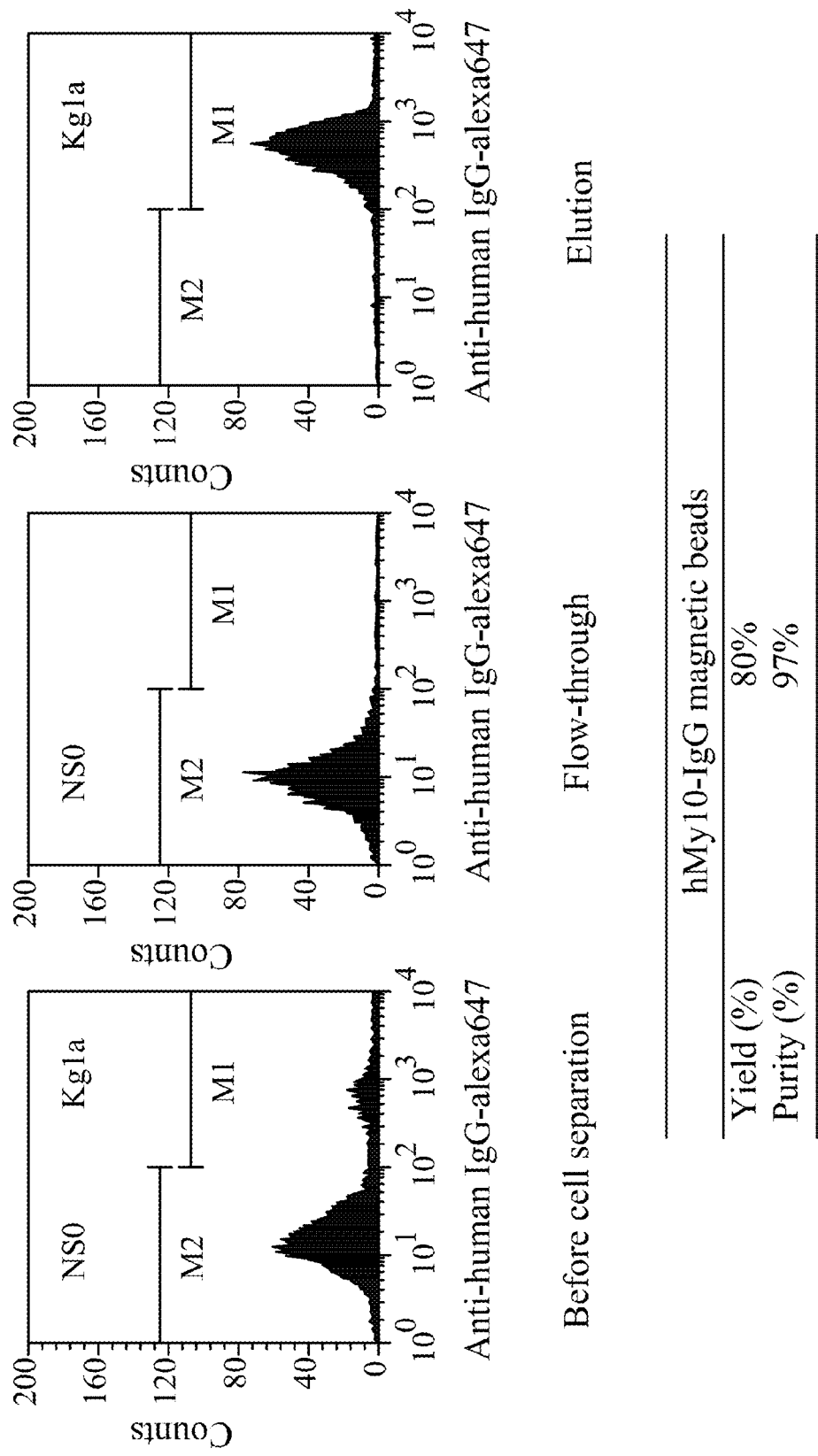
FIG. 7 shows $CD34^+$ cell separation with immunomagnetic beads carrying hMy10 IgG according to an embodiment.

As shown in FIG. 7, the cells before separation contained CD34− NS0 cells with no signal (left side) and CD34+ KG1a cells with signals (right side), indicating that hMy10 IgG bound to KG1a cells but not NS0 cells. In addition, the flow-through fraction collected from the washing buffer when the column was on the magnetic base showed no signal, indicating that these cells were unbound CD34− NS0 cells. In the other side, the target cells collected from the column when the magnetic base was removed showed signals, indicating that these cells were bead-bound CD34+ KG1a cells. This study showed that the immunomagnetic beads carrying the hMY10 IgG antibody were capable of separating CD34− and CD34+ cells in a cell mixture.

In the example, the yield (recovery percentage) of KG1a cells was 80% relevant to the total cell amount initially added into the column. The purity of KG1a cells was 97% relevant to the cell number harvested from the column. The result showed that the beads carrying hMy10 IgG was useful in effective separation of CD34− and CD34+ cells and, in addition, the humanized antibody might further reduce the risk of HAMA reactions if the murine-derived antibody departed from the beads.

H. CD34+ Cell Capture with hMy10 IgG hMy10 IgG was determined for the HSC or EPC capture from the peripheral blood by detecting the capture of CD34+ KG1a cells in a dynamic liquid by using a solid with hMy10 IgG coated thereon. In brief, hMy10 IgG antibodies in various concentrations were coated on the ELISA plate respectively and CD34+ KG1a cells were added therein. The plate was incubated for 1 hour, shaking at 200 rpm. The unbound cells were washed out, and the captured cells were counted cell numbers with Almar Blue.

Figure 8:
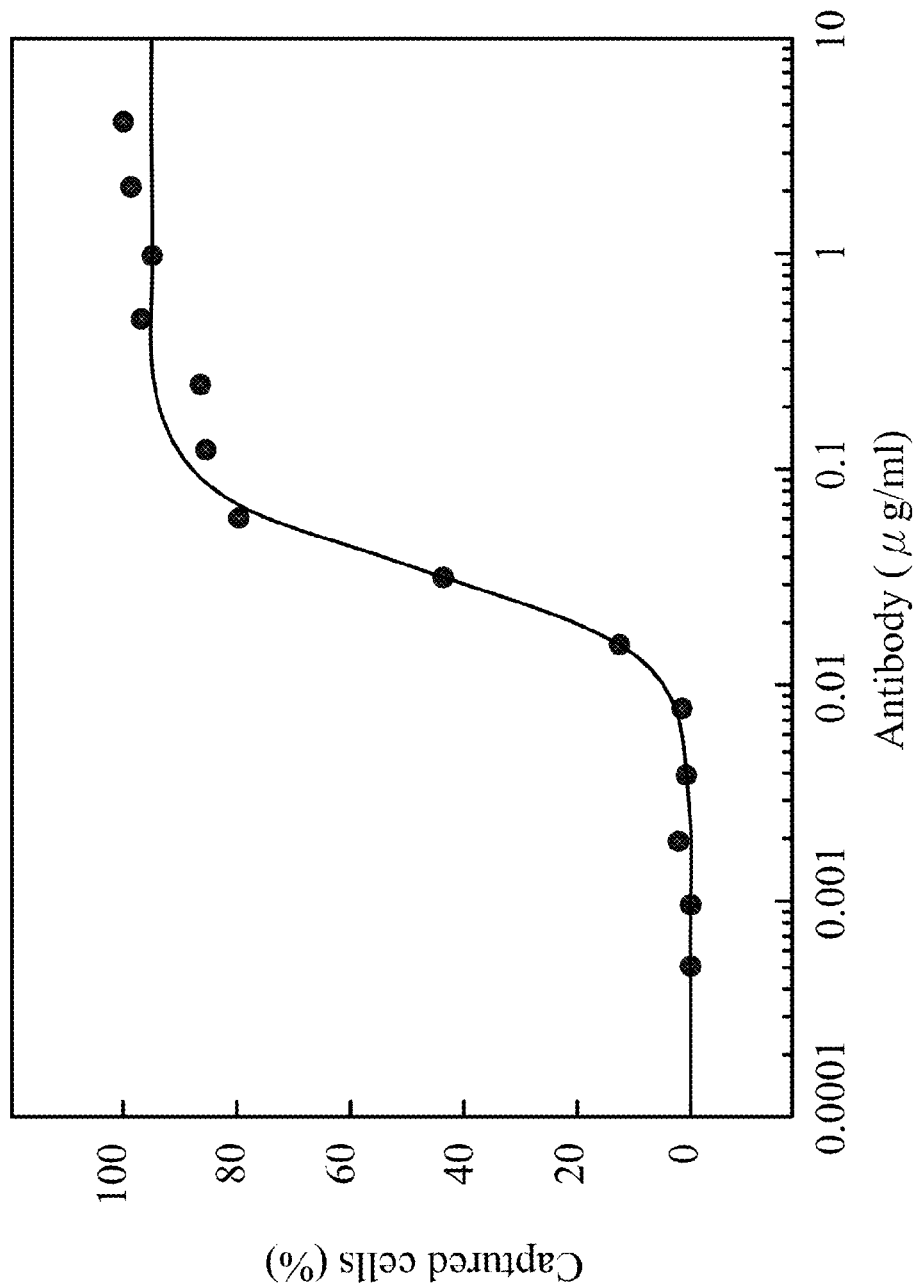
FIG. 8 shows the result of the study on the $CD34^+$ cell capture by using hMy10 IgG according to an embodiment.

As shown in FIG. 8, CD34+ KG1a cells were bound on the ELISA plate in a dose dependent. At the antibody concentration 0.035 μg/ml, still half of the cells were bound. This result proved that hMy10 IgG coated on a solid surface was able to capture CD34+ cells, such as HSCs and EPCs.

Figure 10:
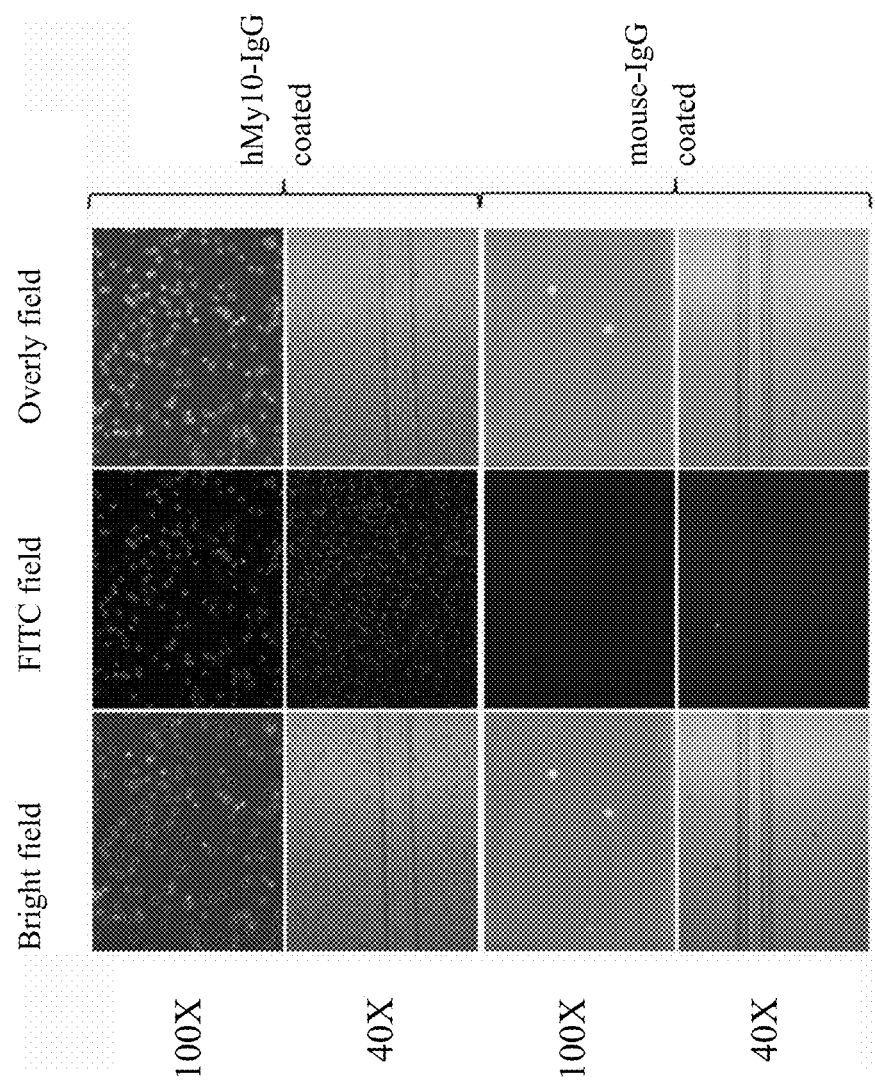
FIG. 10 shows a result of the $CD34^+$ cell capture from the blood flow in a dynamic model by using hMy10 IgG antibody according to an embodiment.

I. CD34+ Cell Capture from the Blood Flow on a Dynamic Modeling hMy10 IgG was determined for the ability of CD34+ KG1a cell capture in a dynamic state like the flowing blood in blood vessels. In the study, a slide comprising microchannels, such as μ-slide (Idibi), was used for modeling the blood flow in blood vessels to analyze the ability of the antibody on the HSC or EPC capture from the peripheral blood. In brief, CD34+ KG1a cells were labeled with green fluorescent PKH167 and mixed with CD34− NS0 cells at a ratio of about 1:10 (KG1a:NS0). The cell mixture was flowed into a μ-slide coated with hMy10 IgG. A μ-slide coated with murine IgG was set as a control. The cells captured on the slide were analyzed under a fluorescent microscope as shown in FIG. 10. The cells on the slide coated with hMy10 IgG all showed green, while the cells on the slide coated with mouse IgG showed nothing. The result showed that the slide coated with hMy10 IgG specifically captured PKH67-labeled green fluorescent CD34+ KG1a cells, while the slide coated with mouse IgG captured no cells. The study proved that hMy10 IgG coated on a solid surface was able to specifically capture cells with the surface antigen CD34, such as HSCs and EPCs, in a fluid state like the flow of blood in blood vessels. Due to the advantages of humanization, hMy10 IgG was allowed to be directly coated on the surface of a medical instrument arranged within the blood vessels, such as coronary stents, avoiding the decrease of antibody activity and the risk of HAMA response induced from murine-derived antibody.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A humanized monoclonal antibody, comprising a heavy chain variable region comprising an amino acid sequence as set forth in SEQ ID NO: 1 and a light chain variable region comprising an amino acid sequence as set forth in SEQ ID NO: 2, wherein the humanized monoclonal antibody specifically binds to a CD34 antigen on a surface of a human cell.

2. The antibody as claimed in claim 1, wherein the human cell comprises a human stem cell.

3. The antibody as claimed in claim 2, wherein the human stem cell comprises a human hematopoietic stem cell (HSC) or human endothelial progenitor cell (EPC).

4. A humanized monoclonal antibody, comprising a heavy chain variable region comprising an amino acid sequence encoded by a nucleotide sequence as set forth in SEQ ID NO: 3 and a light chain variable region comprising an amino acid sequence encoded by a nucleotide sequence as set forth in SEQ ID NO: 4, wherein the humanized monoclonal antibody specifically binds to a CD34 antigen on a surface of a human cell.

5. The antibody as claimed in claim 4, wherein the human cell comprises a human stem cell.

6. The antibody as claimed in claim 5, wherein the human stem cell comprises a human hematopoietic stem cell (HSC) or human endothelial progenitor cell (EPC).

7. A method for cell separation, comprising:
providing a capturing molecule carrying the humanized monoclonal antibody as claimed in claim 1;
mixing the capturing molecule with a biosample, wherein the antibody binds to a CD34 cell-surface antigen in the biosample to form a complex; and
isolating the complex to obtain a cell carrying the surface antigen CD34.

8. The method as claimed in claim 7, wherein the capturing molecule comprises a carrier, functional group or biomolecule.

9. The method as claimed in claim 8, wherein the carrier comprises a bead, microchip or microplate.

10. The method as claimed in claim 8, wherein the functional group comprises an amino group (—$NH_2$), mercapto group (—SH), carboxyl group (—COOH) or hydroxyl group (—OH).

11. The method as claimed in claim 8, wherein the biomolecule comprises a biotin, avidin or streptavidin.

12. The method as claimed in claim 9, wherein the bead comprises an iron oxide particle (TOP) or superparamagnetic iron oxide particle (SPIO).

13. The method as claimed in claim 7, wherein the cell carrying the surface antigen CD34 comprises a human stem cell.

14. The method as claimed in claim 13, wherein the human stem cell comprises a human hematopoietic stem cell (HSC) or human endothelial progenitor cell (EPC).

15. An imaging agent, comprising the humanized monoclonal antibody as claimed in claim 1 and a labeling material binding to the humanized monoclonal antibody.

16. The imaging agent as claimed in claim 15, wherein the labeling material comprises a color material or radioactive material.

17. The imaging agent as claimed in claim 16, wherein the color material comprises a fluorochrome, fluorescent protein, bioluminescence, quantum dot, iron oxide magnetic bead or superparamagnetic iron oxide bead.

18. The imaging agent as claimed in claim 17, wherein the fluorochrome comprises a fluorescein isothiocyanate (FITC), Alexa Fluor dye or Cyanine dye.

19. The imaging agent as claimed in claim 17, wherein the fluorescent protein comprises a phytochrome-based near-infrared fluorescent protein (iRFP).

20. The imaging agent as claimed in claim 17, wherein the bioluminescence comprises a firefly luciferase (Fluc) or Gaussia luciferase (Gluc).

21. The imaging agent as claimed in claim 16, wherein the radioactive material comprises $^{90}Y$, $^{111}In$ or $^{131}I$.

22. The imaging agent as claimed in claim 15, for use in cell fluorescence or luminescence, quantitative positron emission tomography (PET), computed tomography (CT scan), radionuclide imaging or magnetic resonance imaging (MRI).

\* \* \* \* \*

SEQUENCE LISTING

```
<160> NUMBER OF SEQ ID NOS: 4

<210> SEQ ID NO 1
<211> LENGTH: 117
<212> TYPE: PRT
<213> ORGANISM: Artificial
<220> FEATURE:
<223> OTHER INFORMATION: Heavy chain V-region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser His
            20                  25                  30

Gly Val His Trp Val Arg Gln Ala Pro Gly Lys Gly Leu Glu Trp Leu
        35                  40                  45

Gly Val Ile Trp Gly Ala Gly Arg Thr Asp Tyr Asn Ala Ala Phe Ile
    50                  55                  60

Ser Arg Leu Ser Ile Ser Arg Asp Ile Ser Lys Ser Gln Val Tyr Leu
65                  70                  75                  80
```

```
Gln Met Asn Ser Leu Arg Ala Glu Asp Thr Ala Val Tyr Tyr Cys Ala
                85                  90                  95

Arg Asn Arg Tyr Glu Ser Tyr Phe Asp Tyr Trp Gly Gln Gly Thr Leu
            100                 105                 110

Val Thr Val Ser Ser
        115

<210> SEQ ID NO 2
<211> LENGTH: 113
<212> TYPE: PRT
<213> ORGANISM: Artificial
<220> FEATURE:
<223> OTHER INFORMATION: Light chain V-region

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Leu Thr Phe Gly Gln Gly Thr Lys Val Glu Ile Lys
            100                 105                 110

Arg

<210> SEQ ID NO 3
<211> LENGTH: 351
<212> TYPE: DNA
<213> ORGANISM: Artificial
<220> FEATURE:
<223> OTHER INFORMATION: Heavy chain V-region

<400> SEQUENCE: 3
gaggtgcagc tggtggaatc cggaggagga ctggtgcagc caggaggatc cctgaggctg      60
tcttgcgccg tgtctggttt cagtctgaca agccacggcg tgcattgggt caggcaggct     120
cctgaaaagg gactggagtg gctggtgtgt atctggggag ctgggagaac cgactataac     180
gccgctttta tttctcggct gtctatcagt cgcgatatta gcaaatccca gtctacctg      240 cagatgaaca gtctgagagc cgaggacacc gctgtgtact attgtgctag aatagatac      300 gaaagctatt tcgattactg gggccaggga accctggtga cagtgagctc c              351

<210> SEQ ID NO 4
<211> LENGTH: 340
<212> TYPE: DNA
<213> ORGANISM: Artificial
<220> FEATURE:
<223> OTHER INFORMATION: Light chain V-region

<400> SEQUENCE: 4
gacatccaga tgacccagag tcctagctcc ctgtctgcca gtgtgggcga tcgggtgacc      60
attacatgcc gctctagtca gaacctggtg cactccaacg gaaatacata cctgcattgg     120
```

-continued

| | | | | |
|---|---|---|---|---|
| tatcagcaga | agcccgggaa | agctcctaag | ctgctgatct | acaaagtgtc caataggttc | 180 |
| tctggagtgc | cagacaggtt | tagcgggtcc | gggtctggca | cagagttcac tctgaccatt | 240 |
| agctccctgc | agccagaaga | ttttgccact | tactattgta | gtcagagcac acacgtgccc | 300 |
| ctgactttcg | gccagggaac | caaagtggag | atcaagcggc | | 340 |